United States Patent
Raghuvanshi et al.

(10) Patent No.: US 6,586,005 B1
(45) Date of Patent: Jul. 1, 2003

(54) EXTENDED RELEASE FORMULATION OF ETODOLAC

(75) Inventors: Rajeev S. Raghuvanshi, New Delhi (IN); Ashok Rampal, Amritsar (IN); Himadri Sen, Gurgaon (IN)

(73) Assignee: Ranbaxy Laboratories Limited, New Delhi (IN)

( * ) Notice: Subject to any disclaimer, the term of this patent is extended or adjusted under 35 U.S.C. 154(b) by 0 days.

(21) Appl. No.: 09/648,949

(22) Filed: Aug. 25, 2000

(30) Foreign Application Priority Data

Sep. 10, 1999 (IN) ........................ 1210/DEL/99

(51) Int. Cl.$^7$ ................................. A61K 9/22
(52) U.S. Cl. .................. 424/468; 424/400; 424/439; 424/464; 424/465; 424/489
(58) Field of Search ................ 424/464, 439, 424/489, 400, 465, 468

(56) References Cited

U.S. PATENT DOCUMENTS

| 3,939,178 | A | | 2/1976 | Demerson et al. | |
|---|---|---|---|---|---|
| 4,663,345 | A | | 5/1987 | Mullane et al. | |
| 4,704,285 | A | | 11/1987 | Alderman et al. | |
| 4,742,076 | A | | 5/1988 | Mullane et al. | |
| 4,966,768 | A | * | 10/1990 | Michelucci et al. | 424/468 |
| 5,206,025 | A | * | 4/1993 | Courteille et al. | 424/464 |
| 5,614,220 | A | * | 3/1997 | Hirakawa et al. | 424/461 |
| 5,861,173 | A | * | 1/1999 | Nishioka et al. | 424/474 |

FOREIGN PATENT DOCUMENTS

| WO | WO-9939698 | * | 8/1999 | ............ A61K/9/20 |
|---|---|---|---|---|

* cited by examiner

Primary Examiner—Thurman K. Page
Assistant Examiner—Robert M. Joynes
(74) Attorney, Agent, or Firm—Jayadeep R. Deshmukh; William Hare; George E. Heibel

(57) ABSTRACT

A sustained release formulation of etodolac for once daily administration is described.

8 Claims, No Drawings

EXTENDED RELEASE FORMULATION OF ETODOLAC

FIELD OF THE INVENTION

The present invention relates to a sustained release formulation of etodolac for once daily administration.

BACKGROUND OF THE INVENTION

Etodolac (1,8-diethyl-1,3,4,9-tetrahydropyrano [3,4-b] indole-1-acetic acid or a therapeutically acceptable salt thereof) is disclosed in U.S. Pat. No. 3,939,178. It has been reported to have analgesic and anti-inflammatory properties. It has also been reported to be effective in the treatment of gout by lowering uric acid blood levels in humans (U.S. Pat. No. 4,663,345) and in the treatment of rheumatoid arthritis by lowering rheumatoid factor blood levels (U.S. Pat. No. 4,742,076).

Etodolac is approved for the management of signs and symptoms of osteoarthritis, rheumatoid arthritis and for the management of pain. The conventional dosing regimen is 800 mg to 1200 mg given in 2–4 divided doses. This regimen can cause problems of compliance due to lack of patient convenience. It is well known to those skilled in the art that sustained release systems result in a decrease in frequency of administration thereby improving patient compliance. Furthermore, sustained released drug delivery systems produce constant therapeutic plasma levels of active ingredients as compared to fluctuations seen with multiple doses of a conventional formulation. However, development of a sustained release formulation of etodolac effective for 24 hours or suitable for once-a-day administration poses problems due to a very low aqueous solubility of Etodolac which is pH independent below pH 3. The solubility then gradually increases with increasing pH up to 5 and then linearly increases with increasing pH up to 7. A thirty-fold difference between solubility at pH 5 to pH 7 has been observed.

The problem of poor solubility of Etodolac in the acidic media has been addressed by Michelucci et al. by the addition of a release rate modifying agent for maintaining an alkaline microenvironment pH within the tablet. U.S. Pat. No. 4,966,768 describes a sustained release dosage form of Etodolac for once-a-day administration. The addition of a release rate modifiers ensures that pH dependent solubility is minimized throughout the gastrointestinal tract. An admixture of a hydrophilic polymer, hydroxypropyl methylcellulose and a hydrophobic polymer, ethyl cellulose is used for sustaining the release of the drug from the dosage form. The use of a hydrophobic polymer retards the dissolution of the poorly soluble and hydrophobic drug, etodolac, in acidic media thus necessitating the use of release rate modifiers.

U.S. Pat. No. 4,704,285 discloses the use of fine particle sized hydroxypropyl cellulose ether composition for delaying the release of the active composition from a tablet longer upon contacting an aqueous acidic environment at 37° C. compared to a chemically identical but coarser particle sized hydroxypropyl cellulose ether composition. This formulation is not suitable for drugs like etodolac which are poorly soluble in the acidic media.

SUMMARY OF THE INVENTION

An object of the present invention is to provide a sustained release dosage form of etodolac suitable for once daily administration comprising a carrier base material which comprises only hydrophilic polymers wherein no release rate modifying agents are present.

In accordance with the present invention, there is provided a sustained release dosage form suitable for once-a-day administration of Etodolac comprising etodolac and a carrier base material, wherein the carrier base material comprises one or more multiple viscosity grades of a hydrophilic polymer such as hydroxypropyl cellulose.

DETAILED DESCRIPTION OF THE INVENTION

The etodolac used in the present invention is preferably micronized to increase its total surface area and improve its solubility. Hydroxypropylcellulose (HPC) is a partially substituted poly (hydroxypropyl) ether of cellulose which is commercially available under the trade names Klucel™ (Aqualon), Methocel™ (Dow Chemical Co.), and Nisso HPC™. In accordance with the present invention, the carrier base material preferably comprises one or more viscosity grades of HPC. More preferably, hydroxypropyl cellulose is selected from the viscosity grades of 6.0 to 10.0 centipoise (HPC-L) and 150–400 centipoise (HPC-M) for a 2% aqueous solution at 20° C. HPC-L is present from about 5–40% w/w of the formulation or more preferably from 5–20% w/w of the formulation and HPC-M is present from about 5–25% w/w of the formulation or more preferably from 5–15% w/w of the formulation. HPC-L is a rapidly swellable material and is responsible for controlling the initial release of the drug from the dosage form. HPC-M controls the rate of drug release over an extended period of time. It is the appropriate ratio of the two polymers that provides the desired in vitro profiles and the once daily pharmacokinetic profiles. The combined proportion of the carrier base material in the dosage form of the invention can range from 5–65% by weight or more preferably from about 10–35% by weight.

According to the present invention, the pharmaceutical composition may additionally contain conventional pharmaceutical excipients such as diluents, binders, disintegrants, lubricants, coloring agent, etc. According to a preferred embodiment of the present invention, lactose is used as the filler and polyvinyl pyrrolidone (PVP) as the binder.

According to invention, the pharmaceutical composition is preferably in the form of tablets. The tablet is preferably film coated.

The following examples are illustrative only and are not intended to limit the effective scope of the present invention.

EXAMPLE 1

| Ingredient | mg/tablet |
| --- | --- |
| Etodolac | 600 |
| Lactose monohydrate | 166 |
| Hydroxypropyl cellulose (L) | 70 |
| Hydroxypropyl cellulose (M) | 150 |
| PVP K30 | 24 |
| Mg stearate | 10 |
| Talc | 10 |
| Aerosil 200 | 10 |
| Total weight | 1040 |

-continued

| Time (Hrs.) | Cumulative percent drug released |
|---|---|
| 1 | 7.5 |
| 2 | 15.1 |
| 4 | 32.2 |
| 6 | 48.5 |
| 8 | 63 |
| 10 | 75 |
| 12 | 85 |
| 14 | 97 |

Method of manufacture: Etodolac, HPC-L, HPC-M and lactose were sized and dry blended for 20 minutes. The mix was then granulated with solution of PVP. The granules were dried in a fluidized bed drier, dry sized and blended with magnesium stearete, talc and Aerosil 200. The final blend was tableted and coasted with Opadry.

EXAMPLE 2

| Ingredient | mg/tablet |
|---|---|
| Etodolac | 600 |
| Lactose monohydrate | 166 |
| Hydroxypropyl cellulose (L) | 50 |
| Hydroxypropyl cellulose (M) | 120 |
| PVP K30 | 24 |
| Mg stearate | 10 |
| Talc | 10 |
| Aerosil 200 | 10 |
| Total weight | 990 |

| Time (Hrs.) | Cumulative percent drug released |
|---|---|
| 1 | 11.7 |
| 2 | 22.8 |
| 4 | 43.3 |
| 6 | 61.0 |
| 8 | 75.7 |
| 10 | 92.5 |
| 12 | 100.7 |

The method of manufacture was the same as described in Example 1.

EXAMPLE 3

| Ingredient | mg/tablet |
|---|---|
| Etodolac | 600 |
| Lactose | 186 |
| Hydroxypropyl cellulose (L) | 70 |
| Hydroxypropyl cellulose (M) | 110 |
| PVP K30 | 24 |
| Mg stearate | 10 |
| Talc | 10 |
| Aerosil 200 | 10 |
| Total weight | 1020 |

-continued

| Time (Hrs.) | Cumulative percent drug released |
|---|---|
| 1 | 3.5 |
| 2 | 10.8 |
| 4 | 21.3 |
| 6 | 44.3 |
| 8 | 64.1 |
| 10 | 87.7 |
| 12 | 101.5 |

The method of manufacture was the same as described in Example 1.

EXAMPLE 4

| Ingredient | mg/tablet |
|---|---|
| Etodolac | 800 |
| Lactose | 165 |
| Hydroxypropyl cellulose (L) | 150 |
| Hydroxypropyl cellulose (M) | 75 |
| PVP K30 | 24 |
| Mg stearate | 10 |
| Talc | 10 |
| Aerosil 200 | 10 |
| Total weight | 1044 |

| Time (Hrs.) | Cumulative percent drug released |
|---|---|
| 1 | 9.1 |
| 2 | 22.6 |
| 4 | 46.9 |
| 6 | 69.8 |
| 8 | 87.2 |
| 10 | 99.4 |
| 12 | 102.3 |
| 14 | 102.8 |

The method of manufacture was the same as described in Example 1.

EXAMPLE 5

| Ingredient | Mg/tablet |
|---|---|
| Etodolac | 600 |
| Lactose | 155 |
| Hydroxypropyl cellulose (L) | 135 |
| Hydroxypropyl cellulose (M) | 85 |
| PVP K30 | 24 |
| Mg stearate | 10 |
| Talc | 10 |
| Aerosil 200 | 10 |
| Total weight | 1029 |

| Time (Hrs.) | Cumulative percent drug released |
|---|---|
| 1 | 10.4 |
| 2 | 22.2 |
| 4 | 44.6 |
| 6 | 62.3 |
| 8 | 75.6 |
| 10 | 85.2 |
| 12 | 92.9 |
| 14 | 99.4 |

The method of manufacture was the same as described in Example 1.

All the examples described herein illustrate that even in the absence of a release rate modifying agent, use of hydrophilic polymers resulted in a similar rate of drug release as described in the example of U.S. Pat. No. 4,966,768.

While the present invention has been described in terms of its specific embodiments, certain modifications and equivalents will be apparent to those skilled in the art and are intended to be included within the scope of the present invention.

What is claimed is:

1. A sustained release dosage form composition suitable for once-a-day administration comprising etodolac and a carrier base material, where the carrier base material comprises hydroxypropyl cellulose which is a HPC-L having a viscosity grade ranging from 6.0–10 centipoise and present at about 5–40% w/w of the formulation; and a second hydroxypropyl cellulose which is a HPC-M having a viscosity grade ranging from 150–400 centipoise and present at about 5–25% w/w of the formulation, viscosity being measured in a 2% aqueous solution at 20° C.

2. The composition of claim 1, wherein the carrier base material is present from about 5–65% by weight of the formulation.

3. The composition of claim 2, wherein the carrier base material is present from 10–35% by weight of the formulation.

4. The composition of claim 1 wherein the pharmaceutical dosage form is a tablet.

5. The composition of claim 4, wherein the tablet is film coated.

6. The composition of claim 1, wherein the pharmaceutical dosage form further comprises conventional pharmaceutical excipients including diluents, binders, lubricants.

7. The composition of claim 6, wherein the diluent is lactose.

8. The composition of claim 6, wherein the binder is polyvinylpyrrolidone.

* * * * *

UNITED STATES PATENT AND TRADEMARK OFFICE
CERTIFICATE OF CORRECTION

PATENT NO.    : 6,586,005 B1
DATED         : July 1, 2003
INVENTOR(S)   : Rajeev S. Raghuvanshi, Ashok Rampal and Himadri Sen It is certified that error appears in the above-identified patent and that said Letters Patent is hereby corrected as shown below:

<u>Title page,</u>
Item [56], References Cited, U.S. PATENT DOCUMENTS, add
-- 5,958,445   9/28/99   Humber et al. -- and -- 6,106,862   8/22/00   Chen et al. --.

Signed and Sealed this

Sixteenth Day of September, 2003

JAMES E. ROGAN
*Director of the United States Patent and Trademark Office*